United States Patent [19]

Fry

[11] Plant 4,056

[45] May 31, 1977

[54] MUSCADINE GRAPE

[76] Inventor: Byard Owens Fry, 612 Terrace St., Griffin, Ga. 30223

[21] Appl. No.: 610,576

[22] Filed: Sept. 5, 1975

[51] Int. Cl.[2] ..... A01H 5/03

[52] U.S. Cl. ..... Plt./47

[58] Field of Search ..... Plt./47

[56] References Cited

U.S. PATENT DOCUMENTS

P.P. 3,686 2/1975 Triplett ..... Plt./47

*Primary Examiner*—Robert E. Bagwill

*Attorney, Agent, or Firm*—Stanley L. Tate

EXEMPLARY CLAIM

1. The new and distinct hybrid plant variety of the muscadine grape as described and illustrated which is primarily distinguished as to novelty by the unique combination of a very vigorous vine, very large fruit of a dark almost black color wherein said fruit occurs in large clusters of individual berries having a diameter of from about 1 inch to about 1-3/16 inch and the fruit sugar content of the individual berries ranges from about 17.8 to about 22.5 percent.

1 Drawing Figure

The present invention relates to a new and distinct variety of muscadine grape plant which was originated by crossing the variety "Fry." with an unnamed seedling, the former being the seed parent and the latter being the pollen parent.

The general objective of the breeding was to produce an improved variety of muscadine grape plant the fruit of which would have a high sugar content and a dark almost black color which matures in mid season as well as having a very vigorous and attractive plant habit and good resistance to disease which produces high fruit yields which characteristics are outstanding in this new variety and which distinguish it from its parents, as well as from all other varieties of muscadine varieties of which the applicant is aware.

In comparison with its seed parent "Fry", the plant of the new variety produces fruit which is larger and contains an average of up to about 23.5 percent sugar per individual berry which is generally higher than the fruit sugar content of "Fry". Further, the fruit yield of the new variety is always at least equal to that of "Fry" but generally exceeds the fruit yield of the seed parent by an average of from one-half to 1 ton per acre, the average yield of the "Fry" variety being approximately two and one-half tons per acre and the average yield of the new variety being approximately 4 tons per acre.

As compared with the unnamed pollen parent, the plant of the new variety has larger fruit clusters, larger individual berries, a higher fruit sugar content and higher average yields per acre.

Asexual reproduction of the new variety by layering as performed at Brooks, Ga., shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of this character.

The following is a detailed description of the new variety.

Species: *Vitis rotundifolia.*
Type: Vine; seedling; for fruit production.
Seed Parent: "Fry"
Pollen Parent: Unnamed seedling.
Propagation: Holds its distinguishing characteristics through succeeding propagation by layering.
Locality where grown and observed: Brooks, Ga.
Fruit borne: Usually in large clusters, of eight to 12 berries, but sometimes singly.
Fruit size: 1 inch to 1-3/16 inch in diameter; large.
Fruit color: Dark almost black group 202A with some russeting.
Fruit Maturity: Late August to mid October.
Sugar Content Individual Berry: 17.8 to 23.5 percent.
Shape: Spherical to ovoid.
Reproductive Organs: Pistillate variety not self pollenating.
Growth:
*Habit.*—Vine requires support.
*Growth.*—Very vigorous from 6 to 10 feet per year.
*Canes.*—Heavy caliper.
Disease resistance: Good resistance to mildew and black rot as compared to other varieties grown under comparable cultural conditions at Brooks, Ga.
Pulp:
*Color.*—Purple Group 189A.
*Texture.*—Tender and juicy.
Seeds:
*Average diameter.*—3/16 in.
*Average seeds per berry.*—3.30.
Leaf Color: Green Group 137A.

All color designation numbers refer to the Royal Horticultural Society Color Chart, London, England.

This description was made from a vine of the new variety bearing ripe fruit in late August at Brooks, Ga.

What is claimed is:

1. The new and distinct hybrid plant variety of the muscadine grape as described and illustrated which is primarily distinguished as to novelty by the unique combination of a very vigorous vine, very large fruit of a dark almost black color wherein said fruit occurs in large clusters of individual berries having a diameter of from about 1 inch to about 1-3/16 inch and the fruit sugar content of the individual berries ranges from about 17.8 to about 22.5 percent.

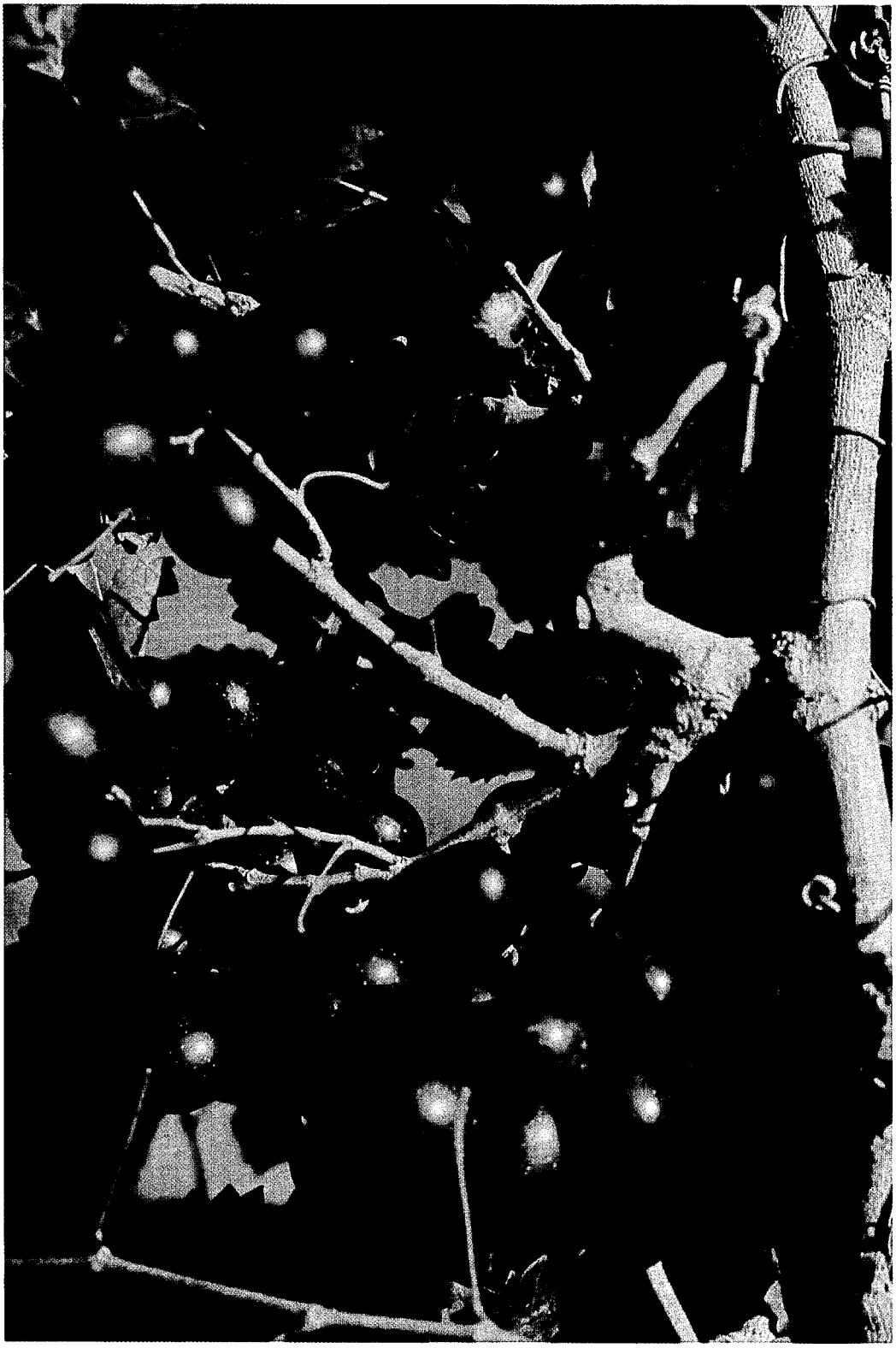

* * * * *